(12) United States Patent
Busin et al.

(10) Patent No.: US 8,410,191 B2
(45) Date of Patent: Apr. 2, 2013

(54) THERMOCHROMIC MATERIAL FOR DENTAL IMPRESSION AND METHOD

(75) Inventors: Tiziano Busin, Badia Polesine (IT); Massimo Rossi, Grignano Polesine (IT); Francesco Callegaro, Borsea (IT)

(73) Assignee: Zhermack S.p.A., Badia Polesine (IT)

( * ) Notice: Subject to any disclaimer, the term of this patent is extended or adjusted under 35 U.S.C. 154(b) by 528 days.

(21) Appl. No.: 11/917,483

(22) PCT Filed: Jun. 7, 2006

(86) PCT No.: PCT/IB2006/001485
§ 371 (c)(1),
(2), (4) Date: Dec. 13, 2007

(87) PCT Pub. No.: WO2006/134437
PCT Pub. Date: Dec. 21, 2006

(65) Prior Publication Data
US 2008/0206713 A1    Aug. 28, 2008

(30) Foreign Application Priority Data

Jun. 15, 2005    (EP) .................................. 05425428

(51) Int. Cl.
*A61K 6/10*    (2006.01)
*A61K 8/72*    (2006.01)

(52) U.S. Cl. ...................................... 523/109; 523/105

(58) Field of Classification Search .................. 523/115, 523/109
See application file for complete search history.

(56) References Cited

U.S. PATENT DOCUMENTS

| | | | | |
|---|---|---|---|---|
| 5,596,025 | A | * | 1/1997 | Oxman et al. ................ 523/109 |
| 5,637,628 | A | * | 6/1997 | Kamohara et al. ............ 523/109 |
| 6,093,755 | A | * | 7/2000 | Kamohara et al. ............ 523/118 |
| 6,559,200 | B1 | | 5/2003 | Kamohara et al. |
| 6,670,436 | B2 | * | 12/2003 | Burgath et al. ............... 526/213 |
| 6,706,218 | B2 | | 3/2004 | Lucht et al. |
| 2002/0152929 | A1 | | 10/2002 | Burgath et al. |
| 2003/0122113 | A1 | * | 7/2003 | Senga et al. .................. 252/586 |
| 2004/0072653 | A1 | * | 4/2004 | Minuto et al. .................. 482/49 |
| 2005/0004305 | A1 | * | 1/2005 | Yamada et al. ............... 524/588 |
| 2005/0250620 | A1 | | 11/2005 | Minuto et al. |

FOREIGN PATENT DOCUMENTS
WO    WO 9927895 A2  *  6/1999
WO    WO 2005/028524 A1   3/2005

* cited by examiner

*Primary Examiner* — Peter F Godenschwager
*Assistant Examiner* — David Karst
(74) *Attorney, Agent, or Firm* — Pearne & Gordon LLP

(57) ABSTRACT

The present invention relates to a thermochromic material for dental impression, capable of reversibly changing color depending on the temperature at which said material is found, a method for its preparation and the use thereof. Said material includes a bicomponent silicone composition in combination with at least a thermochromic pigment.

19 Claims, 3 Drawing Sheets

THERMOCHROMIC MATERIAL FOR DENTAL IMPRESSION AND METHOD

SUMMARY OF THE INVENTION

The present invention relates to a thermochromic material for dental impression, able to reversibly colour change depending on the temperature at which said material is found, a method for its preparation and the use thereof.

Said material includes a bicomponent silicone composition in combination with at least a thermochromic pigment.

TECHNICAL FIELD OF THE INVENTION

The most used materials for taking the dental impression generally consist in silicone-type bicomponent compositions, to be mixed just before the use.

Amongst the silicone compounds used for the preparation of said compositions, the so-called RTV-2 (Room Temperature Vulcanization) silicones are preferred. Once mixed and placed in the patient's mouth, said compositions set themselves through a cross-linking process, which occurs by means of different mechanisms, such as, for instance, condensation or addition mechanisms, depending on the type of the used silicones (condensation silicones and addition silicones, respectively).

The rate of the cross-linking reaction of said silicone compositions is significantly influenced by the temperature, as shown, by way of example, in the enclosed FIG. 1. From the graphs reported in said figure, it results evident how any temperature variations, also relatively moderate (from 23° C. to 35° C.), remarkably increase the rate of setting of the silicone mixture.

Usually, the required tests for individuating the setting time to be indicated in the use instructions of a material for dental impression are carried out by thermostating the sample of said material at 23±2° C. However, in the general operating conditions, the storage temperatures are the most dissimilar, as they depend on a series of factors, such as, for instance: the place, the season, the user habits. Therefore, the setting times shown in the use instructions are only indicative and, depending on the operating temperature, some evident deviations may occur, with respect to what shown in the instructions themselves.

Moreover, also the temperature rise at which the material for dental impression is subjected, once applied inside the patient's mouth, may be sufficient to significantly modify the setting time of said material.

By way of example, the graph of the enclosed FIG. 2 points out that within the mouth, the temperature of a silicone composition with a soft consistency (putty) changes from initial 24° C. to about 34° C. in 3 min. and therefore it results evident that the temperature rise of the material is not instantaneous.

Furthermore, the temperature within the mouth is not necessarily uniform; accordingly, once applied, the material for dental impression can often undergo different temperatures depending on the zone of the mouth in which it is used.

At the current circumstances of the knowledge, in the technical field of the taking of dental impressions lacks the possibility of obtaining in an effective, quick, simple and inexpensive way information concerning both the temperature found by a material for dental impression and the course of the temperature at which said material is subjected, once introduced in the patient's mouth.

Said information would be very useful to the dentist, both for establishing the optimal time of the procedure relating to the taking of the impression, and for modifying the timing of the various operations to be carried out inside the patient's mouth during the taking of the impression, if necessary.

Therefore, a material for dental impression capable of directly transmitting said information to the user, in a real time, would be extremely useful. Materials for dental impression having the features above-mentioned are not known.

KNOWN ART

U.S. Pat. No. 5,596,025 discloses a material for dental impression wherein a chromatic variation of a non reversible type shows the occurred setting of said material.

The colour change is not obtained with reversible thermochromic pigments, but with dyes which stably change the colouring through a final chemical modification of the dye itself. In this kind of material, the final colour variation only denotes the occurrence of the setting of said material and it does not give any information either about its starting temperature or about the need of accelerating, or not, the application procedure of the material itself.

U.S. Pat. No. 6,670,436 discloses resins for dental restoration (non-silicone material), i.e. for a fixed-type applications, wherein a thermochromic pigment has been introduced.

The colour variation due to the pigment is used for removing the excess of resin applied, or when it is necessary to subsequently remove the restoration itself.

DESCRIPTION OF THE INVENTION

Therefore, there is the need for the provision of a material for dental impression able to transmit to the user, in a real time, information relating to the temperature that said material meets.

An object of the present invention is to give a proper answer to the need above-mentioned.

This and other objects, which will result apparent from the following detailed description, have been attained by the Applicant, which has unexpectedly found that it is possible to prepare a material (thermochromic) for dental impression, able to reversibly colour change depending on the temperature that said material meets. Such thermochromic material is prepared by opportunely mixing a silicone bicomponent composition for dental impression with an effective quantity of at least a thermochromic pigment.

The above thermochromic material for dental impression forms an object of the present invention, as it is reported in the enclosed independent claim.

A method for preparing the above thermochromic material for dental impression forms another object of the present invention, as it is reported in the enclosed independent claim.

The use of the aforesaid material for preparing thermochromic dental impressions constitutes a further object of the present invention, as it is reported in the enclosed independent claim.

The use of at least a thermochromic pigment for the preparation of a thermochromic material for dental impression constitutes another object of the present invention, as it is reported in the enclosed independent claim.

A thermochromic dental impression constitutes a further object of the present invention, as it is reported in the enclosed independent claim.

A method for carry out thermochromic dental impressions constitutes a further object of the present invention, as it is reported in the enclosed independent claim.

Preferred embodiments of the present invention are reported in the enclosed independent claims.

Advantageously, the colour change of the material for dental impression of the present invention, depending on the temperature, has resulted reversible, thanks to the use of thermochromic pigments.

To said pigments, having the ability of reversibly changing colour depending on the temperature, belong substances of different nature and chemical structure, such as, for example:
a)—inorganic and organometallic materials;
b)—intrinsically thermochromic organic systems;
c)—indirectly thermochromic systems.

For the purposes of the present invention, the pigments belonging to the systems of group c) have revealed particularly preferred.

Said systems consist of composite materials including at least a chromophoric material, which reacts to the changes caused by the heat in the physical environment in which said material is found, by reversibly changing colour.

Typically, the chromophores used in said systems are pH-sensitive compounds, and the pH of the medium containing them changes according to the temperature variation.

A number of pH-sensitive chromophores is known. Usually, said compounds can be easily synthesized and can be modified so as to give a wide range of colour tone.

The composite thermochromic pigments aforementioned include three components:
  a pH-sensitive dye;
  a weakly acid proton donor, which acts as a colour developer;
  a non-volatile hydrophobic solvent.

In order to obtain the desired effect, the components of the just described system are mixed in opportune ratios and usually are provided in an encapsulated form (microencapsulated) for protecting said system in its applications.

In this way, the pigments result protected from the surroundings and maintain their thermochromatic features unchanged.

Moreover, the microencapsulation helps to remarkably decrease the possible toxicity of some of said systems.

The microencapsulation is a technique well known to the person skilled in the art and is carried out with methodologies and equipments commonly diffused and used in a formulation technique. For example, the encapsulation for a commercial use is carried out by means of standard techniques, such as the coacervation or the interfacial polymerization.

The more generally used pH-sensitive dyes (often referred as colour generators) belong to the spirolactones class, for instance diaryl phtalides or fluorans.

The opening of the colourless lactone ring occurs by protonation from the weak acid, with the formation of the coloured form.

Many weakly acid compounds can be used as colour developers; amongst the most commercially important, the bisphenol A is to be mentioned, which develops brilliant and contrasting colours.

The preferred co-solvents are fatty acids with a low melting point, amides and alcohols. During the preparation of the thermochromic pigments, colour generator, colour developer and co-solvent are melted together and subsequently cooled down to give the coloured pigment.

Said coloured pigments afford a series of advantages, such as:
  colour change within a restricted temperature interval (few degrees);
  possibility of modifying the colour change temperature by opportunely changing the co-solvent;
  possibility of carrying out a wide range of colours, from yellow to red, blue, green and black.

The pigment is coloured when is in a solid form, at temperatures lower than the melting point of the co-solvent, whereas, in a liquid form, it shows a decrease or a loss of the colouring.

Therefore, the normal colour transition involves the change from the coloured form to the uncolored one, with the increasing of the temperature. However, by accurately selecting the type of pH-sensitive dye, it is also possible to obtain a change from a colour to another colour.

At this respect, it is also possible to use mixtures of thermochromic pigments having different melting points and therefore different temperatures of colour changing.

In this case, when one of the mixture components melts and becomes colourless, the colour of the component with the higher melting point emerges.

Amongst the thermochromic pigments which can be advantageously used for the purposes of the present invention, there may also be mentioned those systems containing liquid-crystalline derivatives of the cholesterol. Said derivatives are known; for example, they are disclosed in U.S. Pat. No. 6,670,436, from column 3, line 56 to column 4, line 6.

Other thermochromic pigments which can be advantageously used for the purposes of the present invention are based on polythiophenes, such as for example, those disclosed in U.S. Pat. No. 6,706,218. One of the advantages relating to the use of said polythiophene thermochromic pigments is that the same do not need the microencapsulation, being stable and generally not much toxic.

In the choice of the kind of pigment, or mixture of thermochromic pigments, the person skilled in the art will take into due account especially the possible negative effects which the dispersion of such pigments within the silicone die may cause on the maintenance of the properties of thermochromatic variation of the pigments, as well the possible negative effects which said pigments may exert on the cross-linking ability of the used silicone compounds.

With respect to the chromatic variations, particularly preferred are those mainly evident, such as for example from black, blue, red or yellow to colorless or another colour that can be easily recognized from the former.

In a preferred embodiment of the invention, two different thermochromic pigments, that colour change at different temperatures are combined: for example, a pigment which changes colour at 25° C. and one that changes colour at 35° C. In this way, the material for dental impression containing the above mixture of pigments is able to give indications both about the starting temperature (that is the one at which said material is found after mixing of the components, before its introduction within the patient's mouth) and about the end temperature reached in the mouth of the patient.

In a particularly preferred embodiment of the invention, more than two thermochromic pigments, changing their colours at different temperatures, are combined. In this way, a colour change almost continuous is obtained with the gradual increase of the temperature of the material for dental impression in the mouth of the patient.

With respect to the possible temperature intervals, the thermochromic pigments having colour change in an interval between 0° C. to 40° C. are preferred; preferably, from 10° C. to 37° C.; more preferably, from 15° C. to 37° C.

The concentration of the pigment, or the mixture of thermochromic pigments must be such to make clearly perceptible the chromatic colour change/s.

Said concentration is between 0.01% to 3% by weight, with reference to the total weight of the material for dental impression, according to the intensity of the starting colour that one desires to impart to said material; preferably, from 0.05% to 1.5%; more preferably, from 0.1% to 0.5%.

Thermochromic pigments that can be used for the purposes of the present invention can be selected among those commercially available.

By way of non limiting example, said pigments can be selected among those identified as:

Chromazone®, available from Thermographic Measurement Ltd; Chromicolor®, produced from Matsui Shikiso Chemical Co.; Plasol®, available from Kelly Chemical Co., Reversatherm°, produced from Keystone Aniline Co., whose catalogues are widely diffused and well known to those skilled in the art.

In another preferred embodiment of the invention, the thermochromic pigments are opportunely combined with normal, non-thermochromic pigments, so as to obtain particular colour combinations and variations: for example, from violet to red or blue, or from green to yellow or blue. In this way, it is possible to widen, as one wishes, the range of colours also usable at the highest temperatures, when normally the thermochromic pigment tends to discolour.

As for the bicomponent material for dental impression, as it is known, said material consists in two different silicone compositions (usually called: composition (A), catalyst, and composition (B), base), which are kept in discrete packagings and mixed together just before the use.

In the bicomponent silicone compositions for addition, the two components A) and B) are mixed together in a varying mutual volumetric ratio.

Normally, said ratio is 1:1, but it can also be different (non limiting examples are 5:1, 2:1, 4:1, 10:1, others, or vice versa).

The mixing of the two compositions A) and B) can occur manually, by extruding the material from a little tube or from a cartridge equipped with a static mixer, or by means of an automatic extruder/mixer.

The compositions A) and B) preferably include a mixture of diorganopolysiloxanes having triorganosiloxy end groups, wherein at least one of the three radical groups is a vinyl group.

Polymers of this kind are preferably described with the formula:

$$CH_2=CH(-SiR^1R^2O)_n-SiR^1R^2-CH=CH_2,$$

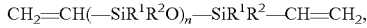

wherein $R^1$ and $R^2$ represent a monovalent hydrocarbon, substituted or not substituted radical. Generally, in $R^1$ and $R^2$ double bonds are not present, but a partial substitution can also be present. Examples of preferred $R^1$ and $R^2$ groups are the methyl, ethyl, phenyl, vinyl or 3,3,3-trifluoropropyl radicals.

Particularly preferred is the methyl radical, which can be present at 100% or in lower fractions.

n represents an integer, whose value is such that the polymer viscosity, measured at 23° C., is included from 50 mPas to 1.000.000 mPas; preferably, from 200 mPas to 100.000 mPas.

The compositions A) and B) can further include one or more silicone oils of different viscosity, not containing vinyl groups, acting as a plasticizer.

The compositions A) and B) can further include compounds, usually called silicone resins, denoted with the abbreviations MQ or VQM, having Si-vinyl, Si—OH, SiOR, SiH groups.

The composition A) particularly includes a hydrosilylation catalyst.

Preferably, said catalyst is chloroplatinic acid, or a Pt siloxane complex, or a catalyst derived from a metal like Rh or Pd.

The metal content (for example in Pt) is between 5 to 500 ppm, based on the total quantity of composition A).

A metal concentration around 100 ppm is particularly preferred.

The composition B) specifically includes a crosslinker, which preferably is an organopolysiloxane containing at least three Si atoms bound to a hydrogen atom per molecule.

The viscosity of said crosslinker is between 5 mPas to 1.000 mPas; preferably, from 15 mPas to 300 mPas.

The SiH content of the crosslinker is between 0.2 to 10 mmole/g of crosslinker; preferably, from 1.5 to 3 mmole/g.

The SiH total content in the composition B) must be such that the complete reaction of all the vinyl residues present in said composition is assured; preferably, it is present in a slight excess with respect to said vinyl residues.

Both in A) and in B), linear or cyclic polysiloxanes, containing a high concentration of vinyl residues, with the function of controller of the Pt reactivity can be present.

In the bicomponent silicone compositions for condensation, the two compositions A) and B) can be mixed in various ratios.

The composition A), the catalyst, includes at least a crosslinker, a organometallic compound which acts as a catalyst and, preferably, different diluents which can be selected, for example, among non reactive silicone polymers, alkyl aromatic compounds, isoparaffins.

The composition B), base, includes a reactive silicone polymer or a mixture of reactive silicone polymers.

In the composition B), the reactive component includes organopolysiloxane polymers having the general formula:

$$X(-SiR^1R^2O)_n-SiR^1R^2-X,$$

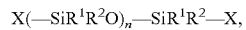

wherein $R^1$ and $R^2$ represent a substituted or not substituted, monovalent hycrocarbon radical. Examples of preferred $R^1$ and $R^2$ groups are the methyl, ethyl, phenyl, vinyl or 3,3,3-trifluoropropyl radicals. Particularly preferred is the methyl radical, which can be present at 100% or in lower fractions.

n represents an integer, whose value is such that the polymer viscosity, measured at 23° C., is included from 50 mPas to 1.000.000 mPas; preferably, from 200 mPas to 100.000 mPas.

X is an hydrolizable Y group, or a hydroxyl group.

Preferred examples of the Y group are, for instance, the oximo, alkoxy, acyloxy groups; particularly preferred is the alkoxy group.

Preferably, the oximo groups are acetophenone oximo, acetone oximo, benzophenone oximo, methyl-ethyl ketoximo, diisopropyl ketoximo.

Preferably, the alkoxy groups are methoxy, ethoxy, n-propoxy, isopropoxy, butoxy, hexyloxy, heptyloxy, octyloxy.

Preferably, the acyloxy groups are formyloxy, acetyloxy, propionyloxy, caproyloxy, stearoyloxy.

The hydroxyl group is particularly preferred. Accordingly, particularly preferred among the reactive silicone polymers are polydiorganosiloxanes with terminal silanol groups.

The composition B) can further include one or more non reactive silicone polymers.

The composition A) includes one or more crosslinkers of formula:

$$R^3_mSi(OR^4)_{4-m},$$

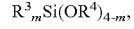

wherein the $R^3$ and $R^4$ groups are defined as the above-mentioned $R^1$ groups;

m are integers and can be 0, 1, 2.

Other possible crosslinkers are polyalkoxysiloxanes with the formula:

$$(R^5O)_3Si[OSi(OR^5)_2]nOSi(OR^5)_3,$$

wherein the $R^5$ groups are defined as the above-mentioned $R^1$ groups.

In the composition A), the catalyst can be selected among those known in the art. Examples of preferred catalysts are: carboxylic acid salts, such as lead 2-ethyl hexanoate, dibutyl-tin dioctanoate, dibutyl-tin diacetate, dibutyl-tin dilaurate, iron 2-hexyl hexanoate, cobalt 2-ethyl hexanoate, manganese 2-ethyl hexanoate, zinc 2-ethyl hexanoate, tin naphthenate, tin oleate, tin caprylate, tin butyrate, titanium naphthenate, zinc naphthenate, cobalt naphthenate, zinc stearate, tetrabutyl titanate, tetra 2-ethylhexyl titanate.

Particularly preferred catalysts for their stability and action rapidity are the or ganostannous siloxanes, which can be obtained with the balancing of the tinmetalorganic compounds with the alkylsilicates; their preparation is known in the field.

Both in the silicone compositions for addition and in those for condensation, the compositions A) and B) can further include: non thermochromic dyes; flavours; hydrocarbon oils; surfactants, such as polysiloxane-polyether copolymers or alkylphenol ethoxylate; opacifiers, such as titanium dioxide.

Both A) and B) can further include a proper quantity of filler.

Said fillers are divided in "extending filler", with a filling function, flowability, appearance, costs reduction, and "reinforcing filler", with a reinforcing function. The former are preferably mineral fillers with BET surface <50 $m^2$/g; for example, quartz, calcium carbonate, fossil meal, iron oxide, aluminum silicates, alumina, fillers made of plastic material, glass balls or milled glass, radiopaque fillers, such as zirconium or tungsten oxides.

The latter, preferably consist in fumed silica or precipitated with a very high BET surface, preferably silanated.

In a preferred embodiment of the present invention, at least one of the compositions A) and/or B) further includes an opportune, effective quantity of at least a heat-conductive filler (thermoconductive fillers), such as, for instance, boron or aluminum nitrides.

Said thermoconductive fillers allow a more fast and homogeneous heat exchange inside the material for dental impression, in particular within the large doughy masses, such as the putties.

Accordingly, the use of the thermoconductive fillers advantageously allow to optimize the efficiency of the thermochromic pigment/s inside all the material for dental impression.

Generally, the concentration of said thermoconductive filler/s is higher than 5% by weight, based on the total weight of the material for dental impression. Preferably, said concentration is higher than 10% by weight; more preferably, higher than 20%; still more preferably, higher than 30%.

In a preferred embodiment of the present invention, the thermoconductive filler/s are added in the composition B) with the bicomponent silicone material for dental impression.

The method for preparing the thermochromic material for dental impression of the present invention substantially includes dispersing in the more homogenous way an effective quantity of pigment, or mixture of thermochromic pigments in at least one of the silicone-based compositions forming said material.

Said dispersion is carried out, for example, with vertical planetary mixers or double-zeta horizontal mixers, or in an extruder, according to techniques known from the skilled in the art, which take into account the viscosity of the employed components, until a homogeneous distribution of the thermochromic pigment/s in the silicone mass is obtained.

The choice of the technology to be used is connected, in a particular way, to the preservation of the structure and the features of the thermochromic pigment/s employed.

The dispersion of the thermochromic pigment/s in at least one of the compositions A) and B) of the bicomponent silicone material for dental impression can be carried out both during the preparation of said compositions, and to the end of the preparation itself.

Preferably, during said dispersion process of the thermochromic pigment/s in the silicone mass, the temperature is controlled at a temperature near to the room temperature, normally not above 40° C. However, if necessary, it is also possible to work at much higher temperatures (for example higher than 60° C. or also higher than 80° C.) depending on the used thermochromic pigment or pigments and their thermal stability.

In a particularly preferred embodiment of the present invention, the thermochromic pigment/s are dispersed in the composition B) of the bicomponent silicone material for dental impression.

The thermochromic material for dental impression according to the present invention advantageoulsy appears as a versatile and interactive material to the user.

The information about the temperature, transmitted in a real time from said material, through the reversible change of the colour, allows the user to obtain indications very accurate on the initial state of the material itself, on its ability to crosslink more or less rapidly with respect to the times shown in the instructions, about the actual progress of the crosslinking process.

By way of absolutely not limiting example only, some cases, in which the use of the thermochromic material for dental impression of the present invention may advantageously affect the manual skill of the user, are given below.

a)—The colour of the material before the use is different from the coloration shown in the instructions; therefore, the starting product has a different temperature with respect to that of reference declared by the producer.

Accordingly, the setting of the material can occur more or less quickly with respect to what is described in the instructions. The dentist will opportunely take into account this fact in the selection of the length of the taking operation of the impression.

b)—After the introduction in the mouth, the more or less rapid colour change gives accurate information about how the material temperature is varying and therefore on the rate at which the crosslinking process (setting) of the product occurs.

In this case, it results then possible to provide the user with instructions like: after the colour change is recommended to not remove the dental impression before n seconds. This possibility allows, for instance, to avoid the deformation of the impression due to the extraction before the complete hardening of the material.

c)—When using the mono-impression technique, with two viscosities or with a single viscosity, the colour variation of the material already placed in the mouth can induce the dentist to change the timing of the different operations, for example, in order to avoid that the insertion of the tray is carried out when the material has already exceed the work time.

d)—It is possible to synchronize the setting time with the colour change. Therefore, the sensory tests for the check of the material setting can be eliminated, with remarkable advantages given from a higher hygiene of the procedure and a higher precision in the impression detection.

e)—When using the mono- or double impression technique, therefore when employing materials with high viscosity, such as for example a putty or a heavy body, it results advantageous the use of a transparent impression-holder. In this way, accurate indications on the setting time from the detection of the colour variation of the material will be obtained.

f)—The use of materials with two or more colours allows a best sight and contrast inside the mouth.

g)—The opportune choice of a darker colour at lower temperatures permits a best reading of the detail, which helps the following laboratory processing from the dental technician.

h)—The casting of the gypsum model can be carried out at an identical temperature to that in the mouth (since the impression colour at the end of the operation is known). In this way, the dimensional variations of the impression itself are compensated, due to the temperature variation.

The thermochromic material according to the present invention has allowed to obtain thermochromic dental impressions particularly accurate and easy to process, thanks to the precise control of the temperature throughout the passages relating to the execution of the same.

The obtaining of said material has been possible thanks to the use of one or more thermochromic pigments, in a proper mixture therebetween.

Said material has therefore also provided the dentist with a best, easier, more accurate and precise method, in order to carry out the dental impression of a patient.

Said method substantially includes:

intimately mixing the two compositions A) and B) of the thermochromic material for dental impression according to the present invention;

introducing in the patient's mouth the mixture obtained;

waiting until the colour of said mixture undergoes the desired final colour change (that is the one which informs about the obtaining of the highest temperature value inside the mouth);

waiting, after said chromathic colour change, for the number of seconds shown in the use instructions of the used material (said number is varying depending on the used thermochromic material);

removing from the patient's mouth the thermochromic dental impression thus obtained.

DETAILED DESCRIPTION OF THE INVENTION

By way of absolutely not limiting illustration of the invention, some examples of preferred embodiments and uses of the same are given below.

The percentages shown in the examples are to be intended as percentages by weight.

The platinum catalyst has been employed as a 1% solution in polydimethylsiloxane.

The normal non-thermochromic pigments are pre-dispersed in concentrated master batches including the pigment in a high concentration in silicone oil, in order to prevent dispersion problems.

The concentrations of said pigments in the master batches are shown in the examples. The thermochromic pigments used in the examples are those produced by Matsui and marketed with the name Chromicolor®; they are also used in master batches in silicone oil at a pigment concentration of 30%.

Example 1

The silicone composition A) is thus constituted:
polydimethylsiloxane 200 mPas 32.5%, polydimethylsiloxane 1.000 mPas 5%, precipitated silica 10%, micronized quartz 24%, aluminum silicate 27%, platinum catalyst 1.5%.

The composition B) is thus constituted:
polydimethylsiloxane 200 in Pas 15%, polydimethylsiloxane 1.000 mPas 2.8%, crosslinker 18%, precipitated silica 12%, micronized quartz 51%, master batch, containing Pigment Yellow 155 at 40%, 0.2%, master batch, containing Chromicolor® Blue 35 (with a nominal temperature of thermochromatic variation of 35° C.), 1%.

The mixing of the two components A) and B) at a temperature of 23° C. provides a green-coloured paste which, introduced in the mouth, rapidly sets by changing its colour to yellow.

After removal from the mouth and cooling at room temperature, the colour of the impression becomes green again.

Example 2

This example shows how the introduction of the thermochromic colour allows to establish a correct way of operation, through the information about the temperature reached from the impression material given from the colour variation.

With the product of the example 1, three cartridges for bicomponent products (each cartridge includes two containers, one for the composition A), one for the composition B) are prepared. The three cartridges are thermostated at three different temperatures: in a refrigerator at 4° C., in a thermostatic bath at 15° C. and at room temperature at 23° C. The three different products then differ for their starting temperature; in order to simulate their slow heating, are extruded by means of the mixing nozzle and respectively deposited on the plate of a Stresstech HR rheometer, Reologica, thermostated at the same temperature of the sample (respectively: 4° C., 15° C., 23° C.). A test, called time sweep (time scanning) is carried out, and simultaneously, the temperature is risen, during a minute, from the initial temperature up to 35° C.

Figure 1:
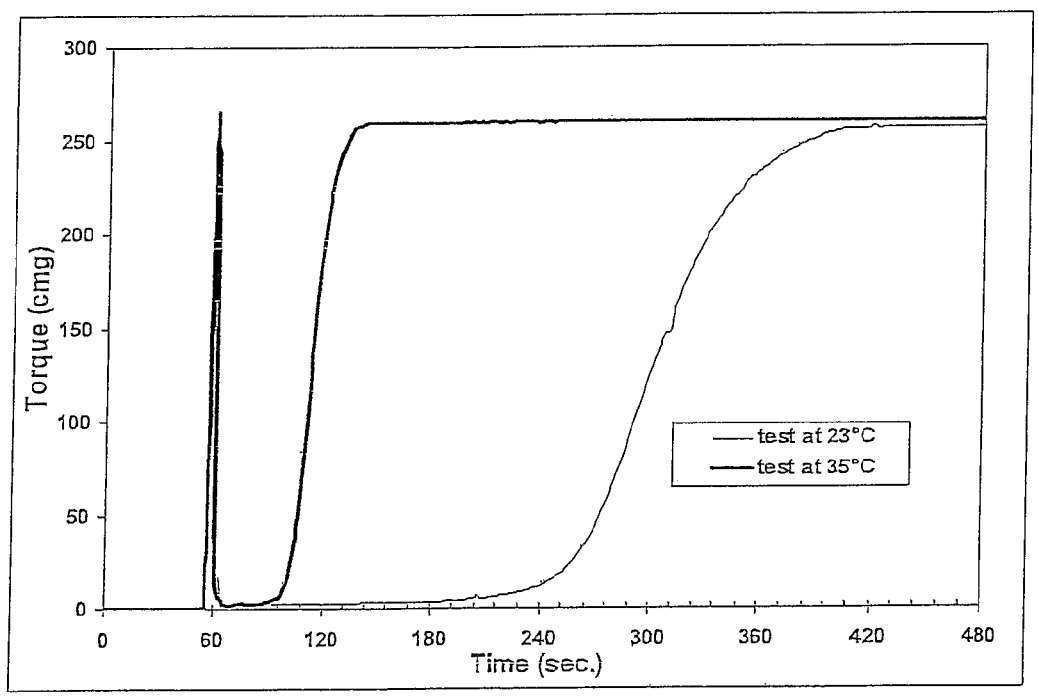
FIG. 1: in this figure, the temperature effect on the setting times of a material for dental impression, based on an addition silicone RTV-2, called Elite HD®, light fast setting, produced by Zhermack, is pointed out (by means of crosslinking curves, obtained with the Brabender cycloviscograph).
Figure 2:
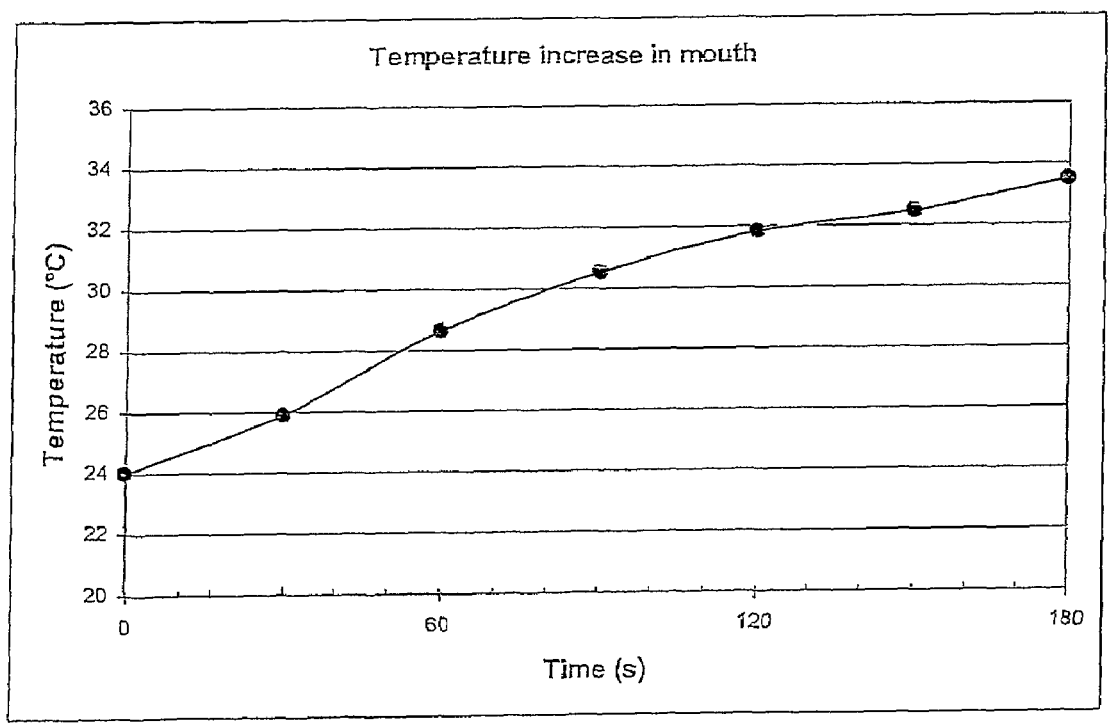
FIG. 2: in this figure, the temperature rise undergone from 10 g of a silicone-based material for dental impression, having a putty consistence is shown, when introduced in the mouth of a patient.
Figure 3:
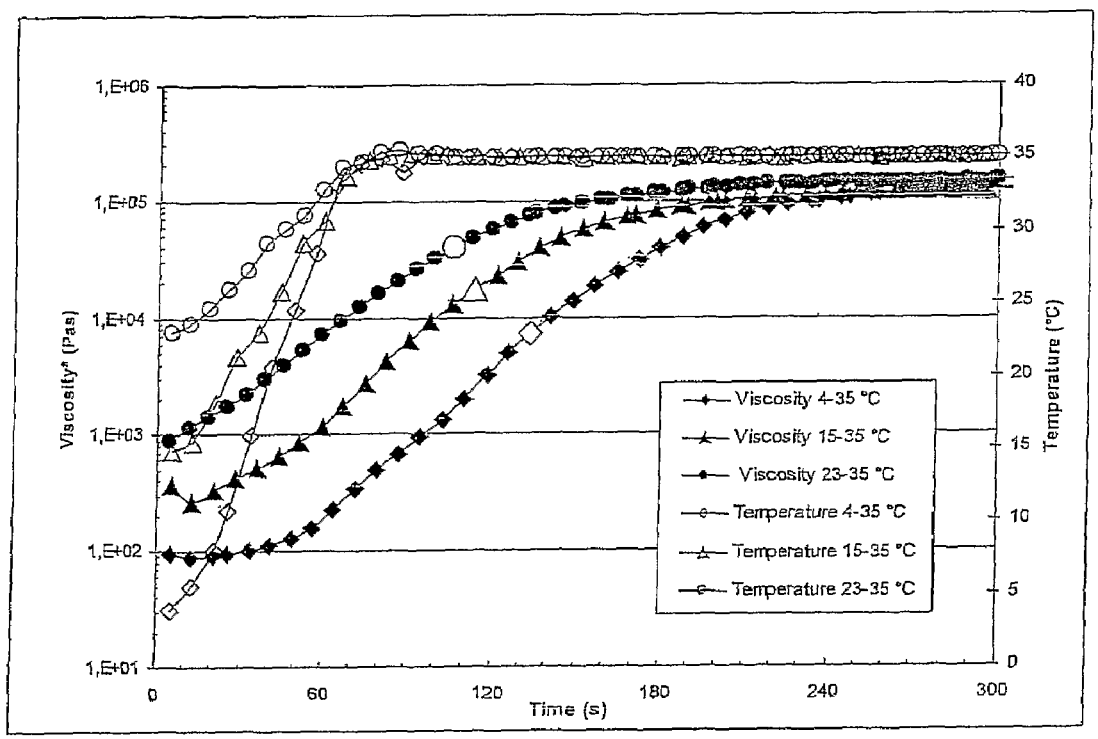
FIG. 3: in this figure, the results of the time sweep test, described in the following Example 2, are graphically reproduced.

In FIG. 3, the time sweep at a varying temperature for the product of the example 1 is reported, i.e. the curves of the temperature rise and the complex viscosity in the three cases are reported.

As it can be observed, when the instrument reaches the temperature of 35° C. the products have not reached the same crosslinking level. In fact, the product thermostated at 4° C. is slowed down with respect to the product thermostated at 23° C. In the viscosity curves of FIG. 3, the moment in which the product changes colour is shown with an empty symbol and with higher dimensions.

From this point on, the time which is left for the complete crosslinking is almost the same in all the three cases.

It is then possible, with the greatest safety, to show, in the use instructions, which is the minimum residence time required in the oral cavity after the chromatic colour change is occurred.

Example 3

The composition A) has the same composition of the example 1.

The composition B) is as follows:
polydimethylsiloxane 200 mPas 15%, polydimethylsiloxane 1.000 in Pas 2.8%, crosslinker 18%, precipitated silica 12%, micronized quartz 51.14%, master batch, containing Pigment Red 172 at 36%, 0.06%, master batch, containing Chromicolor® Blu 35 (with nominal temperature of thermochromatic variation of 35° C.), 1%.

The mixing of the two components A) and B) at a temperature of 23° C. provides a violet-coloured paste which, inserted in the mouth, rapidly sets by changing its colour to light pink.

After removal from the mouth and cooling down at room temperature, the colour of the impression becomes violet again.

Example 4

The composition A) has the same composition of the example 1.

The composition B) is as follows:
polydimethylsiloxane 200 mPas 15%, polydimethylsiloxane 1.000 mPas 2.8%, crosslinker 18%, precipitated silica 12%, micronized quartz 51.19%, master batch containing Pigment Green 7 at 48%, 0.01%, master batch containing Chromicolor® Red 35 (with a nominal temperature of thermochromatic variation of 35° C.), 1%.

The mixing of the two components A) and B) at a temperature of 23° C. provides a grey-coloured paste which, inserted in the mouth, rapidly hardens by changing its colour to green.

After removal from the mouth and cooling down at room temperature, the colour of the impression becomes grey again.

Example 5

The composition A) has the same composition of the example 1.

The composition B) is as follows:
polydimethylsiloxane 200 mPas 15%, polydimethylsiloxane 1.000 mPas 2.8%, crosslinker 18%, precipitated silica 11.8%, micronized quartz 51%, master batch containing Pigment Yellow 155 at 40%, 0.2%, master batch containing Chromicolor® Blue 25 (with a nominal temperature of thermochromatic variation of 23-25° C.), 0.2%, master batch containing Chromicolor® Red 35 (with a nominal temperature of thermochromatic variation of 35° C.), 1%.

The mixing of the two components A) and B) at a temperature of 23° C. provides a brown-coloured paste, if maintained at temperatures lower than 25° C., and orange-coloured if maintained at higher temperatures.

When introduced in the mouth, it rapidly hardens by changing its starting colour (brown or orange) to yellow.

After removal from the mouth and cooling down, the colour of the impression becomes brown or orange depending on that the room temperature is higher or lower than 25° C.

The usefulness of a similar product lies in the fact that according to the storage temperature, the dentist can impart a higher or lower rate to his own work.

Example 6

The following example shows how more accurate results are obtained if, in the steps following the taking of the impression, for instance in the preparation of the cast, one operates in the temperature interval closest to the mouth temperature at which the impression has been taken.

By using the silicone composition of the example 5, a dimensional shrinkage test of the impression is carried out, as described in the ISO 4823 rule. The impression of the reference block is carried out with the material at 23° C. on the block kept in a thermostatic bath at 35° C. Under these conditions, the silicone changes from the brown colour to the yellow one.

The dimensional variation between two rows $d_1$ and $d_2$, which it is measured after 24 hours upon the brown-coloured impression (at 22° C.) is 0.29%, whereas on the orange-coloured impression (at 26° C.) is 0.15% and on the yellow one (at 35° C.) is 0.06%.

Example 7

In this example, the use of thermoconductive fillers is shown, for the purpose of promoting the uniformity of the thermal exchange through large thicknesses of impression material.

The composition A) is as follows:
polydimethylsiloxane 200 mPas 32.5%, polydimethylsiloxane 1.000 mPas 5%, precipitated silica 10%, boron nitride 51%, platinum catalyst 1.5%.

The composition B) is as follows:
polydimethylsiloxane 200 mPas 15%, polydimethylsiloxane 1.000 mPas 2.8%, crosslinker 18%, precipitated silica 12%, boron nitride 51%, master batch, containing Pigment Yellow 155 at 40%, 0.2%, master batch containing Chromicolor® Blue 35 (with a nominal temperature of thermochromatic variation of 35° C.), 1%.

The mixing of the two components A) and B) at a temperature of 23° C. provides a green-coloured slip which, inserted in the mouth, rapidly hardens by changing its colour to yellow in a homogeneous and uniform way in each part of the impression.

After removal from the mouth and cooling down at room temperature, the colour of the impression turns to the original green in a homogeneous way, by confirming the uniformity of the thermal exchange inside the impression material.

The invention claimed is:

1. A thermochromic material for dental impression comprising a bicomponent silicone composition and one or more thermochromic pigments, said bicomponent silicone composition comprising a curable silicone polymer and a crosslinker compound, said one or more thermochromic pigments being present in the material in a concentration effective to permit the material, after crosslinking, to reversibly change color in a temperature dependent manner, said material, before being effectively cured, having a consistency of a dough effective to permit a dental patient to bite down on it and form an effective dental impression, said material being effective for obtaining an effective dental impression from the dental patient and being effectively deformable so that, after the dental impression is made, the material is effectively removable from the patient's mouth.

2. Material according to claim 1, wherein said bicomponent silicone composition further comprises a catalyst.

3. Material according to claim 1, wherein said one or more thermochromic pigments is selected from the group consisting of indirectly thermochromic composite materials, liquid-crystalline derivatives of cholesterol, polythiophenes, and mixtures thereof.

4. Material according to claim 1, wherein said one or more thermochromic pigments is in an encapsulated form.

5. Material according to claim 1, wherein said one or more thermochromic pigments has a color change between 0° C. to 40° C.

6. Material according to claim 1, wherein said material includes two or more thermochromic pigments.

7. Material according to claim 1, wherein said material includes 2 thermochromic pigments which change color at different temperatures.

8. Material according to claim 1, wherein said material further comprises an effective quantity of thermoconductive filler.

9. A method for preparing a thermochromic material for a dental impression, comprising a step of homogeneously dispersing an effective quantity of one or more thermochromic pigments in a bicomponent silicone composition to provide a material according to claim 1.

10. A method according to claim 9, wherein said one or more thermochromic pigments is selected from the group consisting of indirectly thermochromic composite materials, liquid-crystalline derivatives of cholesterol, polythiophenes, and mixtures thereof.

11. A method according to claim 9, wherein said one or more thermochromic pigments is in an encapsulated form.

12. A method according to claim 9, wherein said one or more thermochromic pigments provides a color change between 0° C. to 40° C.

13. The method according to claim 9, wherein said one or more thermochromic pigments provides a color change between 15° C. to 37° C.

14. A method of using a thermochromic material for a dental impression, comprising the steps of providing a quantity of thermochromic material according to claim 1, and preparing a dental impression employing said quantity of thermochromic material.

15. A thermochromic dental impression consisting of a material according to claim 1.

16. A method for preparing a thermochromic dental impression, including:
 intimately mixing a material according to claim 1;
 inserting in a patient's mouth the mixture obtained;
 waiting for a color of said mixture to undergo a desired color change;
 waiting, after said color change, for a number of seconds shown in a use instructions of the used material;
 removing from the patient's mouth the thermochromic dental impression thus obtained.

17. Material according to claim 1, wherein said one or more thermochromic pigments has a color change between 10° C. to 37° C.

18. Material according to claim 1, wherein said one or more thermochromic pigments has a color change between 15° C. to 37° C.

19. The method according to claim 9, wherein said one or more thermochromic pigments provides a color change between 10° C. to 37° C.

* * * * *